United States Patent [19]

Drent

[11] Patent Number: 4,692,548
[45] Date of Patent: Sep. 8, 1987

[54] PROCESS FOR THE PREPARATION OF UNSATURATED COMPOUNDS

[75] Inventor: Eit Drent, Amsterdam, Netherlands

[73] Assignee: Shell Oil Company, Houston, Tex.

[21] Appl. No.: 862,927

[22] Filed: May 14, 1986

[30] Foreign Application Priority Data

Jun. 14, 1985 [GB] United Kingdom ............... 8515139

[51] Int. Cl.$^4$ .................. C07C 67/347; C07C 2/32
[52] U.S. Cl. ................................ 560/202; 502/102; 502/155; 502/165; 502/167; 560/190; 562/590; 562/595; 585/508; 585/510; 585/511; 585/514
[58] Field of Search ............. 560/202; 562/595; 502/102, 155, 165, 167; 585/508, 510, 511, 514

[56] References Cited

U.S. PATENT DOCUMENTS

| | | | |
|---|---|---|---|
| 3,013,066 | 12/1961 | Alderson | 560/202 |
| 3,074,999 | 1/1963 | Rauhut et al. | 560/202 |
| 3,342,853 | 9/1967 | Nemec et al. | 560/202 |
| 4,451,665 | 5/1984 | Nugent | 560/202 |
| 4,485,256 | 11/1984 | McKinney | 560/202 |

FOREIGN PATENT DOCUMENTS 1355917  6/1974  United Kingdom .

OTHER PUBLICATIONS

*Tetrahedron Letters*, No. 4, (1979), 343–344.
*Z. Chem.* 20, (1980), 24.

*Primary Examiner*—Michael L. Shippen
*Assistant Examiner*—Vera C. Clarke

[57] ABSTRACT

The dimerization of acrylate esters and of ethene and the codimerization of acrylate esters with $C_{2-4}$-alkenes or 1,3-butadiene and of 1,3-butadiene with ethene in the presence of:

(a) a Pd and/or Ru compound,
(b) a compound containing one trivalent N or P atom, and
(c) an Ag and/or Cu salt, yields at an increased reaction rate dimers of high linearity, when a quinone is also present.

15 Claims, No Drawings

PROCESS FOR THE PREPARATION OF UNSATURATED COMPOUNDS

FIELD OF THE INVENTION

The invention relates to a process for the dimerization in the liquid phase by reaction of an ethylenically unsaturated compound of the general formula:

in which $R^1$ represents a hydrogen atom, an alkyl group having not more than two carbon atoms, a vinyl group or a hydrocarbyloxycarbonyl group, with an ethylenically unsaturated compound of the general formula:

in which $R^2$ represents a hydrogen atom or a hydrocarbyloxycarbonyl group, with the restriction that, when $R^1$ represents an alkyl group, $R^2$ does not represent a hydrogen atom.

BACKGROUND OF THE INVENTION

It is known from British Patent Specification No. 1,355,917 that methyl acrylate can be dimerized to linear mono-unsaturated dimethyl dicarboxylates in the presence of a divalent palladium complex in combination with a quinone. Such linear esters are important intermediates for the production of polymers. However, this known dimerization proceeds rather slowly.

It is known from *Tetrahedron Letters* No. 4 (1979) 343–344, that methyl acrylate can be dimerized to linear mono-unsaturated dimethyl dicarboxylates in the presence of palladium(II) dichloride complexed with triphenylphosphine. It is stated that the rate of dimerization is increased by adding silver-fluoroborate. The Applicant has found that conversion is low in this known process and that metallic silver is formed.

It is an object of the present invention to provide a process exhibiting an increased rate of reaction and in which a catalyst is used which remains stable, yet producing dimers having a high linearity.

SUMMARY OF THE INVENTION

This invention relates to a process for the dimerization in the liquid phase by reaction of an ethylenically unsaturated compound of the general formula:

in which $R^1$ represents a hydrogen atom, an alkyl group having not more than two carbon atoms, a vinyl group or a hydrocarbyloxycarbonyl group, with an ethylenically unsaturated compound of the general formula:

in which $R^2$ represents a hydrogen atom or a hydrocarbyloxycarbonyl group, with the restriction that, when $R^1$ represents an alkyl group, $R^2$ does not represent a hydrogen atom, which process is carried out in the presence of a catalytic system formed by combining:

(a) a palladium and/or ruthenium compound;
(b) a monodentate ligand which comprises a compound containing one trivalent N or P atom as coordinating atom;
(c) a silver and/or cupric salt having a non-coordinating anion, and
(d) a quinone.

DESCRIPTION OF THE PREFERRED EMBODIMENTS

Palladium compounds which can be used in the process according to the invention are preferably soluble in the reaction medium or form in situ soluble compounds therein. Examples of suitable palladium compounds are palladium nitrate, palladium sulfate, palladium halides and palladium carboxylates, preferably carboxylates of carboxylic acids having not more than 12 carbon atoms per molecule. Palladium carboxylates, in particular palladium acetate, are preferably used.

Further examples of suitable palladium compounds are palladium complexes such as bis(2,4-pentanedionato)palladium, bis(picolinato)-palladium, tetrakis(triphenylphosphine)palladium, tetrakisacetonitrile palladium tetrafluoroborate, bis(tri-o-tolylphosphine)palladium acetate, bis(triphenylphosphine)palladium sulfate, palladium olefin complexes for instance di-μ-chlorodichlorobis(ethylene)dipalladium ($[Pd.C_2H_4Cl_2]_2$), and di-μ-chlorodichlorobis(propylene)dipalladium ($[Pd.C_3H_6.Cl_2]_2$), and palladium-hydride complexes.

Examples of suitable ruthenium compounds are ruthenium(III)-chloride, ruthenium(IV)chloride, ruthenium(III)chloride trihydrate, ruthenium oxides, ruthenium carboxylates such as ruthenium acetate or ruthenium propionate and ruthenium(III)trisacetylacetonate.

The quantity of the palladium and/or ruthenium compound used may vary within wide ranges and is generally in the range between $10^{-6}$ and $10^{-1}$ mol palladium and/or ruthenium compound per mol ethylenically unsaturated compound of formula I. A range between $10^{-5}$ and $10^{-2}$ mol palladium and/or ruthenium compound is preferred.

Monodentate ligands which are used in the process of the invention comprise compounds containing one trivalent N or P atom as coordinating atom, which is preferably bonded to at least one aromatic hydrocarbon group or a compound containing a trivalent N atom, which is a member of a heterocyclic aromatic ring.

Examples of suitable monodentate ligands comprising a compound which contains a trivalent N or P atom bonded to at least one aromatic hydrocarbon group are N,N'-dialkylanilines and phosphines such as N,N'-dimethylaniline, N,N-diethylaniline, N,N'-dibutylaniline, 4-chloro-N,N'-dimethylaniline, 4-ethoxy-N,N'-dimethylaniline, 4-dimethylaminobenzenesulfonic acid, 3-dimethylaminobenzenesulfonic acid, bis(1,1-dimethylethyl) phenylphosphine, dimethylphenylphosphine, cyclohexyldiphenylphosphine, dibutylphenylphosphine, methyldiphenylphosphine, triphenylphosphine, tris(4-tolylphosphine), tris(4-chlorophenyl)phosphine, tris(4-methoxyphenyl)phosphine, tris(3-methoxyphenyl)phosphine, tris(2-methoxyphenyl)phosphine, tris(4-butylphenyl)phosphine, tris(4-triflurophenyl)phosphine, tris(4-fluorophenyl)phosphine and 2-carboxyphenyl diphenylphosphine.

Examples of suitable monodentate ligands comprising a compound which contains a trivalent N atom being part of a heterocyclic aromatic ring are pyridines and quinolines such as pyridine, 2,6-dimethylpyridine, 4-ethylpyridine, 2-methoxypyridine, 2-chloropyridine, 3-chloropyridine, 2,6-dichloropyridine, 2-pyridine carboxylic acid, 3-pyridine carboxylic acid, quinoline, 2-methylquinoline and 2-chloroquinoline.

The use of monodensate ligand which comprises N,N'-dimethylaniline, triphenylphosphine, pyridine or the derivatives thereof is preferred. Very good results have been obtained with triphenylphosphine and with a triphenylphosphine, the phenyl groups of which carry one or more substituents, for example halogen atoms and/or alkyl, aryl, alkoxy, carboxy, carbalkoxy, acyl, trihalogenmethyl, cyano, dialkylamino, sulfonylalkyl and alkanoyloxy groups.

The quantity of monodentate ligand is suitably at least 2 mol per gram atom of palladium and/or ruthenium. A complex of palladium and/or ruthenium with a monodentate ligand may be prepared outside the vessel in which the dimerization is to be effected or, alternatively, in situ by simply adding a suitable compound of palladium, for example palladium acetate or palladium chloride, or of ruthenium, for example ruthenium trichloride, to the monodentate ligand, for example triphenylphosphine.

By "non-coordinating anion" is meant that little or no co-valent interaction takes place between the palladium or ruthenium and the anion (cf. British Patent Application No. 2,058,074).

The non-coordinating anion is preferably derived from an acid having a pKa of less than 3 and, more preferably, less than 2, measured in aqueous solution at a temperature of 18° C.

Examples of non-coordinating anions are derived from sulfonic acids and from acids that can be formed, possibly in situ, by interacting a Lewis acid such as, for example, $BF_3$, $AsF_5$, $SbF_5$, $PF_5$, $TaF_5$ or $NbF_5$ with a Broensted acid such as, for example, a hydrogen halide, in particular HF, fluorosulfonic acid, phosphoric acid or sulfuric acid. Specific examples of acids of the latter type are fluorosilicic acid, $HBF_4$, $HPF_6$ and $HSbF_6$. Examples of usable anions are derived from sulfonic acids such as fluorosulfonic acid and chlorosulfonic acid and the hereinafter specified sulfonic acids. Very good results have been obtained with the anion derived from $HBF_4$.

A preferred group of anions are those derived from acids having the general formula III:

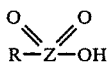

(III)

wherein Z represents sulfur or chlorine and, if Z is chlorine, R represents oxygen and, if Z is sulfur, R represents an OH group or an optionally substituted hydrocarbon group.

When the hereinbefore-stated anions are used in the process according to the invention, the anions of the compounds can be considered to be non-coordinating.

The optionally substituted hydrocarbon group represented by R is preferably an alkyl, aryl, aralkyl or alkaryl group having 1 to 30, in particular 1 to 14, carbon atoms. The hydrocarbon group may, for example, be substituted with the halogen atoms, in particular fluorine atoms. Examples of suitable acids of the general formula III are perchloric acid, sulfuric acid, 2-hydroxypropane-2-sulfonic acid, benzenesulfonic acid, 1- and 2-naphthalensesulfonic acid, p-toluenesulfonic acid and trifluoromethanesulfonic acid, the last two acids being the most preferred.

The molar ratio of silver and/or cupric salt having a non-coordinating anion to palladium and/or ruthenium compound is not critical and may vary within a wide range. Preferably, this molar ratio is in the range of from 1 to 50, and, more preferably, from 2 to 20.

The word "dimerization" as it is used herein, refers to the reaction of two identical compounds as well as the reaction of two different compounds.

The process according to the present invention is particularly suitable for the dimerization of acrylate esters, $R^1$, and $R^2$ in the general formulas I and II, respectively, each representing a hydrocarbyloxycarbonyl group. The hydrocarbyl group in this ester may be an optionally substituted alkyl, optionally substituted cycloalkyl or optionally substituted aryl group and is preferably an alkyl group having not more than 4 carbon atoms. Very good results have been obtained with methyl acrylate. This compound can be quantitatively converted into dimers, i.e. dimethyl 2-hexenedioate, dimethyl 3-hexenedioate, dimethyl 2-methyl-2-pentenediotate and dimethyl 2-methyl-3-pentenedioate. The linearity of these esters, being the sum of the amounts of the first and the second ester, calculated on the sum of the four esters, is usually at least 92%.

The process according to the present invention is also very suitable for (a) reacting an alpha-alkene ($R^1$ in the general formula I representing a hydrogen atom or a methyl or an ethyl group) with an acrylate ester ($R^2$ in the general formula II representing a hydrocarbyloxycarbonyl group), thus producing esters of alkenoic acids of high linearity;

(b) dimerization of ethene, or (c) reacting 1,3-butadiene ($R^1$ in the general formula I representing a vinyl group) with ethylene ($R^2$ in the general formula II representing a hydrogen atom) or with an acrylate ester ($R^2$ in the general formula II representing a hydrocarbyloxycarbonyl group).

The quinone used in the present process may be, for example, a benzoquinone, a naphthoquinone, an anthraquinone or a chrysenequinone. Specific examples of suitable quinones are p-benzoquinone, anthraquinone, 1,4-naphthoquinone and 5,6-chrysenequinone. Very good results have been obtained with p-benzoquinone and substituted derivatives thereof, such as 2,3,5,6-tetrachlorobenzoquinone and 2,3,5,6-tetramethylbenzoquinone.

The molar ratio of quinone to palladium and/or ruthenium compound is preferably in the range of from 100 to 0.1, but molar ratios below or above this range are not excluded. Usually this ratio is above 1.

According to a preferred embodiment of the present invention ethylene is reacted with 1,3-butadiene and a chelate ligand is also combined with the catalytic system, which chelate ligand comprises an organic compound containing as coordinating atoms at least two atoms of Group Va of the Period Table of the Elements which are connected through a chain comprising 2 to 6 carbon atoms. Surprisingly, the presence of this chelate ligand allows a rather high selectivity to linear hexadienes. The Periodic Table of the Elements mentioned herein refers to that shown on the inside of the cover of Handbook of Chemistry and Physics, 61st edition (1980–1981), CRC Press, Inc.

Suitable compounds may be compounds containing two nitrogen atoms which are connected through a chain comprising 2 carbon atoms such as 1,2-ethanediamine compounds for example N,N,N',N'-tetramethyl-1,2-ethanediamine, N,N,N',N'-tetraethyl-2,2-ethanediamine and N,N,N',N'-tetraphenyl-1,2-ethanediamine, heterocyclic diamines for example 1,4-diphenylpiperazine, 1,4-dimethyl-1,4-dihydropyrazine and compounds containing in the molecule a group of the formula:

for example N,N'-1,2-ethanediylidenebisphenylamine, N,N'-1,2-ethanediylidenebis[4-chlorophenylamine], N,N'-1,2-ethanediylidenebis[4-methoxyphenylamine], N-substituted derivatives of 2-pyridinemethanimine, 2,2'-bipyridyl, 4,4'-dimethyl-2,2'-bipyridyl, 4,4'-dichloro-2,2'-bipyridyl, 4,4'-dimethoxy-2,2'-bipyridyl, 1,10-phenanthroline, 5-chloro-1,10-phenanthroline, 4,7-diphenyl-1,10-phenanthroline, 4,7-dimethyl-1,10-phenanthroline, 2,9-dichloro-1,10-phenanthroline, 1,10-phenanthroline-5-sulfonic acid, 4,7-diphenyl-1,10-phenanthrolinedisulfonic acid, and 3,5-cyclohexadiene-1,2-diimine.

Other suitable compounds may be compounds containing two phosphorus atoms, or two arsenic atoms or optionally a phosphorus atom or an arsenic atom in combination with a nitrogen atom which are connected through a chain comprising 2 carbon atoms such as for example 1,2-ethanediylbisdiphenylphosphine, 1,2-ethendiylbisphenylphosphine, 1,2-ethynediylbisdiphenylphosphine, 1,2-ethanediylbisdi(trifluoromethyl)phosphine, 1,2-phenylenebisdiphenylphosphine, 1,2-tetrafluorocyclobutenediylbisdiphenylphosphine, 1,2-hexafluorocyclopentenediylbisdiphenylphosphine, 1,2-octafluorocyclohexenediylbisdiphenylphosphine, 1,4-diphenyl-1,4-diphosphacyclohexane, bis(o-diphenylphosphinophenyl)-phenylphosphine, tris(o-diphenylphosphinophenyl)phosphine, 1,2-phenylenebisdimethylarsine, 1,2-ethanediylbisdiphenylarsine, 1-dimethylamino-2-phenyldiethylphosphine, 8-dimethylarsinoquinoline, 10-methyl-5,10-dihydrophenarsazine, 1,2-tetrafluorophenylenebisdimethylarsine.

Further suitable compounds may be compounds containing at least two nitrogen atoms, phosphorus atoms or arsenic atoms connected through a chain comprising 3 to 5 carbon atoms such as for example N,N,N',N'-tetramethyl-1,3-propanediamine N,N,N',N'-tetramethyl-1,4-butanediamine, 1,3-propanediylbisdiphenylphosphine, 1,4-butanediylbisdiphenylphosphine, bis(bis-3-dimethylarsinopropyl)arsine, tetrakis(3-dimethylarsinopropyl)o-phenylenediarsine.

The compounds preferably used in the catalytic system in the process according to the invention are 1,10-phenanthroline and the derivatives thereof, 2,2'-bipyridyl and the derivatives thereof and bisdiphenylphosphine compounds in which the two phosphorus atoms are connected through a chain comprising 2 or 3 carbon atoms.

The quantity of chelate ligands used in the catalytic system when reacting ethylene with 1,3-butadiene is at least 1.5 mol ligand per mol palladium and/or ruthenium and is preferably not higher than 25 mol ligand per gram atom palladium and/or ruthenium.

The process according to the invention is suitably carried out in an aprotic organic solvent. Examples of suitable solvents are hydrocarbons such as hexane, cyclohexane, octane, cyclo-octene, benzene, toluene, the three xylenes, ethylbenzene and cumene, halogenated hydrocarbons such as chloroform, 1,2-dichloroethane, perfluoroalkanes, chlorobenzene and the three dichlorobenzenes, ethers such as tetrahydrofuran, diethyl ether, 3,6-dioxaoctane, methyl tert-butyl ether and dioxane, esters such as methyl benzoate and the acrylic ester to be dimerized and nitro compounds such as nitromethane and nitrobenzene.

The process according to the invention can be carried out at temperatures of up to 200° C. and preferably in the range between 20° C. and 135° C. The pressure lies between 1 and 100 bar.

The process according to the invention can be carried out batchwise, semi-continuously or continuously.

The invention is further illustrated by means of the following examples which are not to be construed as limiting the invention. Each experiment was carried out in a 250 ml autoclave provided with a magnetic stirrer.

Comparative Experiment A - methyl acrylate

A mixture formed by combining methyl acrylate (30 ml) and [P(C$_6$H$_5$)$_3$]$_2$PdCl$_2$ (0.5 mmol) was stirred for one hour at 70° C. No reaction was observed.

Comparative Experiment B - methyl acrylate

A mixture formed by combining methyl acrylate (30 ml) and [(P(C$_6$H$_5$)$_3$]$_2$PdCl$_2$ (0.5 mmol) and AgBF$_4$ (1.5 mmol) was stirred at 70° C. The conversion of methyl acrylate stopped after 1 hour stirring. The inside wall of the autoclave was covered with a silver mirror. Further results are stated in Table 1.

TABLE 1

| Example | Comparative Experiment | Conversion, %, of methyl acrylate | Turnover, mol methyl acrylate per gram atom Pd per h | Selectivity, %, to dimers | trimers | Linearity %, of dimers |
|---|---|---|---|---|---|---|
|  | B | 20 | — | 93 | 7 | 93 |
| 1 |  | 100 | 120 | 92 | 7 | 92 |
| 2 |  | 100 | 200 | 92 | 8 | 92 |

The dimers consisted of dimethyl 2-hexenedioate, dimethyl 3-hexenedioate, dimethyl 2-methyl-2-pentenedioate and dimethyl 2-methyl-3-pentenedioate. The linearity is the molar percentage of the sum of the two hexenedioates, calculated on the sum of the four dimethyl esters.

EXAMPLE 1 methyl acrylate

By repeating Comparative Experiment B in the presence of p-benzoquinone (2.0 mmol) no silver mirror was observed. The results obtained after 5 h stirring are presented in Table 1.

EXAMPLE 2

METHYL ACRYLATE

By repeating Example 1 except that 3.0 mol of AgBF$_4$ was used, the results presented in Table 1 were obtained. Comparison with Example 1 shows that more AgBF$_4$ has increased the turnover.

Comparative Experiment C - methyl acrylate

No reaction was observed by repeating Comparative Experiment A in the presence of p-benzoquinone (2.0 mmol).

EXAMPLE 3

METHYL ACRYLATE AND ETHENE

The autoclave was charged with methyl acrylate (30 ml), [P(C$_6$H$_5$)$_3$]$_2$PdCl$_2$ (0.5 mmol), AgBF$_4$ (3.0 mmol) and p-benzoquinone (2.0 mmol). Then, ethene was introduced until a partial pressure of 40 bar was reached. After 5 h stirring at 70° C., conversion of methyl acrylate was 85% (turnover 300 mol acrylate per gram atom Pd per h). The product mixture obtained consisted of 65 mol % (methyl 4-pentenoate plus methyl 3-pentenoate plus methyl 2-pentenoate plus methyl 3-methyl-2-butenoate plus methyl 3-methyl-3-butenoate), 30 mol % (1-butene plus 2-butene) and 5 mol % dimers of methyl acrylate, the content of pentenoates plus butenoates, calculated on total dimers derived from methyl acrylate being 93%. The linearity was 94%.

EXAMPLE 4

METHYL ACRYLATE AND PROPENE

By repeating Example 3, except that the ethene was replaced with propene (30 ml), a conversion of 85% of methyl acrylate was observed (turnover 250 mol acrylate per gram atom Pd per h). The product mixture obtained consisted of 60 mol % dimeric esters derived from 1 mol of methyl acrylate and 1 mol of propene (linearity 90%) and 40 mol % dimeric esters derived from 2 mol of methyl acrylate. No dimers derived from 2 mol of propene had been formed.

EXAMPLE 5

METHYL ACRYLATE AND 1-BUTENE

By repeating Example 3, except that the ethene was replaced with 1-butene (30 ml), a conversion of 92% of methyl acrylate was observed (turnover 250 mol acrylate per gram atom Pd per h). The product mixture obtained consisted of 25 mol % dimeric esters derived from 1 mol of methyl acrylate and 1 mol of 1-butene (linearity 70%) and 75 mol % dimeric esters derived from 2 mol of methyl acrylate (linearity 94%). No dimers derived from 2 mol of 1-butene had been formed.

EXAMPLE 6

ETHENE

The autoclave was charged with methyl benzoate (50 ml), [P(C$_6$H$_5$)$_3$]$_2$PdCl$_2$ (0.5 mmol), AgBF$_4$ (3.0 mmol), p-benzoquinone (2.0 mmol) and ethene (40 bar). After 2 h stirring at 70° C. the turnover was 1500 mol ethene per gram atom Pd per h with a selectivity to linear butenes of 96% and to hexenes of 4%.

EXAMPLE 7

METHYL ACRYLATE AND PROPENE

The autoclave was charged with methyl acrylate (15 ml), sulfolane (30 ml), [P(C$_6$H$_5$)$_3$]$_2$Pd Cl$_2$(0.5 mmol), AgBF$_4$ (3.0 mmol), p-benzoquinone (2.0 mmol) and propene (30 ml). After 5 h stirring at 75° C. the conversion of methyl acrylate was higher than 95% and the turnover more than 150 mol acrylate per gram atom Pd per h. The product mixture obtained contained 88 mol % dimeric esters derived from 1 mol of methyl acrylate and 1 mol of propene (linearity 75%) and 12 mol % dimeric esters derived from 2 mol of methyl acrylate.

EXAMPLE 8

METHYL ACRYLATE AND PROPENE

By repeating Example 7, except that the AgBF$_4$ was replaced with silver tosylate (3.0 mmol) and 20 mmol of p-benzoquinone were present, a conversion of methyl acrylate of 95% was observed (turnover more than 150 mol acrylate per gram atom Pd per h). The product mixture obtained contained 90 mol % dimeric esters derived from 1 mol of methyl acrylate and 1 mol of propene (linearity 80%) and 10 mol % dimeric esters derived from 2 mol of methyl acrylate.

EXAMPLE 9

ETHENE

The autocloave was charged with methyl benzoate (50 ml), [P(C$_6$H$_5$)$_3$]$_2$PdCl$_2$ (0.5 mmol) AgBF$_4$ (3.0 mmol), 1,10-phenanthroline (0.5 mmol), p-benzoquinone (2.0 mmol) and ethene (40 bar). After 5 h stirring at 70° C. the conversion of ethene was more than 95%, the turnover being more than 200 mol ethene per gram atom palladium per hour. The product mixture consisted of 80 mol % linear butenes, 18 mol % hexenes and 2 mol % octenes.

EXAMPLE 10

ETHENE

The autoclave was charged with methyl benzoate (30 ml), palladium acetate (0.5 mmol), triphenylphosphine (1.0 mmol), AgCF$_3$SO$_3$ (3.0 mmol), 1,10-phenanthroline (0.5 mmol), p-benzoquinone (20 mmol) and ethene (40 bar). After 5 h stirring at 70° C. a conversion of ethene of more than 95% was observed. The product mixture consisted of 80 mo l% linear butenes, 19 mol % hexenes and 1 mol % octenes.

EXAMPLE 11

ETHENE

The autoclave was charged with methyl benzoate (50 ml), palladium(II) acetate (0.5 mmol), triphenylphosphine (1.0 mmol), 1,10-phenanthroline (0.5 mmol), cupric tosylate (3.0 mmol), p-benzoquinone (20 mmol) and ethene (40 bar). After h stirring at 70° C. the conversion of ethene was 25%. The product mixture consisted of 95 mol % linear butenes and 5 mol % hexenes.

EXAMPLE 12

ETHENE

By repeating Example 11 except that 2,3,5,6-tetrachlorobenzoquinone (20 mmol) was used instead of p-benzoquinone, a conversion of ethene of more than 95% was observed. The product mixture consisted of 80 mol % linear butenes, 19 mol % hexenes and 1 mol % octenes.

EXAMPLE 13

METHYL ACRYLATE AND PROPENE

By repeating Example 7, except that the p-benzoquinone was replaced with 2,3,5,6-tetramethylbenzoquinone, a conversion of methyl acrylate of 100% was observed; the turnover was more than 150 mol acrylate per gram atom Pd per h. The product mixture consisted of 85 mol % dimeric esters derived from 1 mol of methyl acrylate and 1 mol of propene (linearity 80%) and 15 mol % dimeric esters derived from 2 mol of methyl acrylate.

EXAMPLE 14

1,3-BUTADIENE AND ETHENE

The autoclave was charged with palladium(II) acetate (0.5 mmol), triphenylphosphine (1.0 mmol), AgCF$_3$SO$_3$ (3.0 mmol), p-benzoquinone (20 mmol), 1,10-phenanthroline (0.5 mmol), 1,3-butadiene (10 ml) and ethene (40 bar). After 5 h stirring at 80° C. the product mixture consisted of 98 mol % linear butenes, the reaction with 1,3-butadiene being very slow. The conversion of ethene was 25% and the turnover 50 mol ethene per gram atom Pd per h.

EXAMPLE 15

1,3-BUTADIENE AND ETHENE

By repeating Example 14, except that 1.0 mol of 1,10-phenanthroline was present, a product mixture was found consisting of 30 mol % linear hexadienes, mainly trans 2,4-hexadiene and 70 mol % linear butenes.

COMPARATIVE EXPERIMENT D - ETHENE

The autoclave was charged with methyl benzoate (50 ml), palladium(II) acetate (0.5 mmol), triphenylphosphine (1.0 mmol) 1,10-phenanthroline (0.5 mmol), AgCF$_3$SO$_3$ (3.0 mmol) and ethene (40 bar). After 5 h stirring at 70° C. the conversion of ethene was 70%, with a selectivity to linear butenes of 90% to hexenes of 10%.

EXAMPLE 16

ETHENE

By repeating Comparative Experiment E, except that also p-benzoquinone (20 mmol) was present, an ethene conversion of 80% after 1 h with a selectivity to linear butenes of 80% and to hexenes of 20% was found.

EXAMPLE 17

1,3-BUTADIENE AND ETHENE

The autoclave was charged with methyl benzoate (50 ml), [P(C$_6$H$_5$)$_3$]$_2$PdCl$_2$ (0.5 mmol), 1,10-phenanthroline (0.5 mmol), AgCF$_3$SO$_3$ (3.0 mmol), p-benzoquinone (20 mmol), 1,3-butadiene (10 ml) and ethene (40 bar). After 5 h stirring at 70° C. the turnover of ethene was 70 mol per gram atom palladium per hour. The product mixture consisted of equal molar amounts of linear hexadienes and linear butenes.

EXAMPLE 18

METHYL ACRYLATE AND ETHENE

The autoclave was charged with methyl acrylate (50 ml), [P(C$_6$H$_5$)$_3$]$_2$PdCl$_2$ (0.5 mmol), hydrated Cu(BF$_4$)$_2$ (3.0 mmol), p-benzoquinone (20 mmol), and ethene (40 bar). After 5 h stirring at 70° C. the conversion of methyl acrylate was 50% and the turnover 500 mol acrylate per gram atom Pd per h. The product mixture consisted of 50 mol % linear butenes, 45 mol % dimeric esters from 1 mol of methyl acrylate and 1 mol of ethene (linearity 90%) and 5 mol % dimers of 2 mol of methyl acrylate.

Comparative Experiment E - ethene

The autoclave was charged with methyl benzoate (50 ml), palladium(II) chloride (0.5 mmol), silver tosylate (3.0 mmol), p-benzoquinone (20 mmol) and ethene (40 bar). After 5 h stirring at 70° C. only a trace of products was found.

EXAMPLE 19

METHYL ACRYLATE

The autoclave was charged with methyl acrylate (100 ml), a complex (0.5 mmol) consisting of 1 mol of palladium(II) chloride and 2 mol of tri(m-methoxyphenyl)-phosphine, AgBF$_4$ (1.5 mmol) and p-benzoquinone (5.0 mmol). After 10 h stirring at 60° C. a conversion of methyl acrylate of 75% was found (turnover 2000 mol methyl acrylate per gram atom Pd) with a selectivity to dimers of 93% (linearity 92%) and to trimers of 7%.

EXAMPLE 20

METHYL ACRYLATE AND 1,3-BUTADIENE

The autoclave was charged with methyl acrylate (50 ml), 1,3-butadiene (10 ml), [P(C$_6$H$_5$)3]$_2$PdCl$_2$ (0.5 mmol), AgBF$_4$ (3.0 mmol) and p-benzoquinone (20 mmol). After 5 h stirring at 70° C. the conversion of 1,3-butadiene and methyl acrylate were 99% and 50%, respectively, with a selectivity to dimers of 1 mol of 1,3-butadiene and 1 mol of methyl acrylate of 50% (linearity 95%) and to dimers of 2 mol of methyl acrylate of 50% (linearity 94%).

EXAMPLE 21 methyl acrylate and ethene

The autoclave was charged with methyl acrylate (50 ml), ruthenium trichloride (0.5 mmol), triphenylphosphine (1.0 mmol), AgBF$_4$ (3.0 mmol), p-benzoquinone (20 mmol) and ethene (40 bar). After 5 h stirring at 90° C. the turnover of methyl acrylate was 50 mol per gram atom Ru per h. The product mixture consisted of 60 mol % linear butenes, 30 mol % dimers of 1 mol of ethene and 1 mol of methyl acrylate and 10 mol % dimers of 2 mol of methyl acrylate.

EXAMPLE 22 methyl acrylate and 1,3-butadiene

The autoclave was charged with methyl acrylate (50 ml), 1,3-butadiene (10 ml), ruthenium trichloride (0.7 mmol), triphenylphosphine (1.0 mmol), AgBF$_4$ (3.0 mmol) and 2,3,5,6-tetrachlorobenzoquinone (10 mmol). After 5 h stirring at 90° C. the conversion of 1,3-butadiene was 50%. The product mixture consisted of 100% dimers of 1 mol of 1,3-butadiene and 1 mol of methyl acrylate (linearity 95%), no dimers of 2 mol of methyl acrylate being formed.

What is claimed is:

1. A process for dimerization in the liquid phase which comprises reacting an ethylenically unsaturated compound of the formula:

in which $R^1$ represents a hydrogen atom, an alkyl group having not more than two carbon atoms, a vinyl group or a hydrocarbyloxycarbonyl group, with an ethylenically unsaturated compound of the formula:

(II)

in which $R^2$ represents a hydrogen atom or a hydrocarbyloxycarbonyl group, with the restriction that, when $R^1$ represents an alky group, $R^2$ does not represent a hydrogen atom, which process is carried out in the presence of a catalytic system formed by combining:
   (a) a palladium and/or ruthenium compound;
   (b) a monodentate ligand which comprises a compound containing one trivalent N or P atom as coordinating atom;
   (c) a silver and/or cupric salt having a non-coordinating anion, and
   (d) a quinone.

2. The process of claim 1 wherein the monodentate ligand comprises a compound containing one trivalent N or P atom which is bonded to at least one aromatic hydrocarbon group.

3. The process of claim 2 wherein the monodentate ligand comprises triphenylphosphine or a triphenylphosphine with one or more substituents on the phenyl groups.

4. The process of claim 1 wherein the non-coordinating anion is a $BF_4^-$, p-tosylate or $CF_3SO_3^-$ anion.

5. The process of claim 1 wherein the quione is p-benzoquinone or a substituted p-benzoquinone.

6. The process of claim 1 wherein a molar ratio of quinone to palladium and/or ruthenium compound in the range of from 100 to 0.1 is used.

7. The process of claim 1 wherein a molar ratio of silver and/or cupric salt having a non-coordinating anion to palladium and/or ruthenium compound in the range of from 1 to 50 is used.

8. The process of claim 1 wherein a molar ratio of palladium and/or ruthenium compound per mol ethylenically unsaturated compound of formula I in the range between $10^{-6}$ and $10^{-1}$ is used.

9. The process of claim 1 wherein ethylene is reacted with 1,3-butadiene and wherein a chelate ligand is also combined with the catalytic system, said chelate ligand comprising an organic compound containing as coordinating atoms at least two atoms of Group Va of the Periodic Table of the Elements which are connected through a chain comprising 2 to 6 carbon atoms.

10. The process of claim 9 wherein the chelate ligand comprises a compound containing as coordinating atoms two nitrogen atoms connected through a chain comprising two carbon atoms.

11. The process of claim 10 wherein the chelate ligand comprises a compound containing in the molecule a group of the formula:

12. The process of claim 11 wherein the chelate ligand comprises 1,10-phenanthroline or a derivative thereof.

13. The process of claim 9 wherein a molar ratio of chelate ligand to palladium and/or ruthenium compound in the range of from 1.5 to 25 is used.

14. The process of claim 1 wherein $R^1$ in formula I and $R^2$ in formula II each represent an alkyloxycarbonyl group in which the alkyl group has not more than 4 carbon atoms.

15. The process of claim 14 wherein the compounds of formula I and II are methyl acrylate.

* * * * *